US008568141B2

(12) United States Patent
Tanaka et al.

(10) Patent No.: US 8,568,141 B2
(45) Date of Patent: Oct. 29, 2013

(54) LINEARLY MOTORIZED DENTAL SYRINGE

(75) Inventors: Fumio Tanaka, Chuo-ku (JP);
Mitsuhiro Haraguchi, Chuo-ku (JP);
Yoshihiko Kawasaki, Chuo-ku (JP);
Mutsumi Shibuya, Chuo-ku (JP);
Kiyoshi Wakabayashi, Matsudo (JP);
Yoshinori Katoh, Matsudo (JP); Renji Hayashi, Matsudo (JP)

(73) Assignee: Showa Yakuhin Kako Co., Ltd., Chuo-ku, Tokyo (JP)

( * ) Notice: Subject to any disclaimer, the term of this patent is extended or adjusted under 35 U.S.C. 154(b) by 202 days.

(21) Appl. No.: 13/377,284

(22) PCT Filed: Jun. 26, 2009

(86) PCT No.: PCT/JP2009/061704
§ 371 (c)(1),
(2), (4) Date: Dec. 9, 2011

(87) PCT Pub. No.: WO2010/150396
PCT Pub. Date: Dec. 29, 2010

(65) Prior Publication Data
US 2012/0088206 A1 Apr. 12, 2012

(51) Int. Cl.
*A61C 5/04* (2006.01)
*A61M 5/00* (2006.01)

(52) U.S. Cl.
USPC .......................................... 433/90; 604/207

(58) Field of Classification Search
USPC ..................... 433/89, 90, 103, 114; 604/155, 604/207–211
See application file for complete search history.

(56) References Cited

U.S. PATENT DOCUMENTS

| 2,882,704 | A | 4/1959 | Quackenbush |
| 5,921,966 | A | 7/1999 | Bendek et al. |
| 5,957,896 | A | 9/1999 | Bendek et al. |
| 7,476,216 | B2 * | 1/2009 | Takatsuka et al. ............ 604/131 |
| 8,409,148 | B2 * | 4/2013 | Fiechter et al. .............. 604/197 |
| 8,444,607 | B2 * | 5/2013 | Mounce et al. .............. 604/218 |
| 2002/0077601 | A1 | 6/2002 | Kawagishi et al. |
| 2004/0176725 | A1 * | 9/2004 | Stutz et al. .................... 604/155 |
| 2005/0137534 | A1 | 6/2005 | Hommann |
| 2005/0137571 | A1 | 6/2005 | Hommann |
| 2005/0209569 | A1 * | 9/2005 | Ishikawa et al. .............. 604/207 |
| 2009/0137967 | A1 | 5/2009 | Hommann |
| 2009/0221973 | A1 | 9/2009 | Hommann |

FOREIGN PATENT DOCUMENTS

| JP | 11-104240 A | 4/1999 |
| JP | 2001-70444 A | 3/2001 |
| JP | 2005-531348 A | 10/2005 |
| JP | 2007-330572 A | 12/2007 |
| WO | WO 2004/004809 A1 | 1/2004 |

* cited by examiner

*Primary Examiner* — Matthew F DeSanto
(74) *Attorney, Agent, or Firm* — Chapman and Cutler LLP

(57) ABSTRACT

A linear cartridge-type motorized dental syringe has a plunger rod aligned with a drive shaft of a motor, the externally threaded plunger rod movable longitudinally, but not rotatably, relative to the casing, a cylindrical body rotated by the shaft, a nut having arm-like nut halves with internal threads engaging external threads on the rod, a locking ring for rotation around an axis of the rod and for longitudinal movement between a rearward position where the ring forces the threads on the nut halves to engage the threads on the rod, and forward where the ring releases engagement of the threads, pusher pins for moving the ring rearward when the cartridge holder is inserted, and a spring for pushing the locking ring back to the forward position, with rotation of the cylinder body resulting in rotative motion of the nut around the rod to move it forward.

7 Claims, 5 Drawing Sheets

LINEARLY MOTORIZED DENTAL SYRINGE

TECHNICAL FILED

The present invention relates to a motorized dental syringe for use in injection of injection solution such as anesthetic in dental treatment and more particularly, to a linear cartridge-type motorized dental syringe.

BACKGROUND ART

Injection of the anesthesia in the dental treatment has been carried out by using various cartridge-type motorized syringes in recent years. One of them was developed by assignors of this application and has been put widely to practical use. Reference 1 can be made to Japanese patent application directed to such a cartridge-type motorized syringe and published under Publication 2001-70444. The cartridge-type motorized syringe comprises an electric motor with reduction gears, a pinion adapted to be rotated through a planetary reduction gears by the motor, and a plunger rod having a rack meshed with the pinion to move forwardly the plunger rod from its initial retracted position, thereby pushing a plunger rubber fitted in an anesthetic filled cartridge so that the anesthetic can be ejected from the cartridge through a needle attached to the cartridge while piercing a rubber plug fitted in the cartridge at its tip. The forward movement of the plunger rod for the injection of anesthetic into the oral cavity is performed at extremely low speeds such as 30 mm/60 seconds, 30 mm/100 seconds and 30 mm/200 seconds, for example. Upon completion of the injection, the plunger rod is required to return to the initial retracted position. This can be achieved by pushing the plunger rod back to the initial retracted position quickly by the hand of a dental surgeon after the operative connection between the pinion meshed with the rack on the plunger rod and the drive mechanisms is cut off.

There were two problems to be solved in this motorized dental syringe. One of them was cracking of the glass tube wall of the cartridge by contact of the tip of the plunger rod with the inner surface of the glass tube wall, due to offset of the plunger rod from the center of the rubber plunger in the cartridge while the plunger rod pushes the rubber plunger with the tip end thereof. The inventors of this application found that one of the causes of the cracks lay in the rack and pinion mechanism incorporated in the syringe. Since force of 300 N (about 30 kg) is exerted on the plunger rod during injection to eject the anesthetic during injection, the geared motor deviates in a direction escaping from the load imposed on the motor so that some force is applied to the rack on the plunger rod to maintain the rack relative to the pinion driven by the motor at 90 degrees. As a result, the tip of the plunger rod deviates from its given straight position. Namely, the tip of the plunger rod contacts the rubber plunger in the cartridge at a position deviated from the center of the rubber plunger. As the other problem, the above syringe had disadvantages of complicating the drive mechanism for the rack and pinion because of use of the planetary reduction gears as a reduction gear, and that the means for cutting off the operative connection between the pinion and the drive mechanism was also complicated in structure.

PRIOR ART

PATENT REFERENCE 1: Publication for patent application JP 2001-70444

DISCLOSURE OF THE INVENTION

An object of the invention is to provide a linear cartridge-type motorized dental syringe capable of solving the above mentioned problems by aligning a driving shaft of a geared motor serving as a prime mover linearly with a plunger rod and making advance drive of the plunger rod possible with a simple mechanism.

Another object is to provide a linear cartridge-type motorized dental syringe capable of pushing the plunger rod simply back to its initial retracted position with a simple mechanism after completion of injection.

The object of the invention can be achieved by providing a linear cartridge-type motorized dental syringe comprising a housing in which a motorized syringe unit is fixedly incorporated, the motorized syringe unit comprising a casing provided with a coupling having at the front end thereof, a cylindrical space in which a cartridge holder is inserted, the coupling functioning to detachably couple the inserted cartridge holder to the syringe unit, and a motor with a reduction gear (referred to as a geared motor) secured to the rear end of a fixed casing, an externally threaded plunger rod located in alignment with the axis of a drive shaft of the geared motor, the plunger rod being movable longitudinally of the casing but not rotatable relative to the casing, a rotating cylindrical body located coaxially in the casing and operatively connected to the drive shaft of the geared motor such that it can be rotated by the drive shaft, a nut including a pair of arm-like nut halves protrusive forward beyond the forward end of the rotating cylindrical body and having on the forward inner surfaces internal threads adapted to engage the external threads on the plunger rod, a locking ring located for rotation around the axis of the plunger rod and for longitudinal movement between a rearward position wherein it forces the internal threads on the arm-like nut halves to engage the external threads on the plunger rod and a forward position wherein it functions to release the mutual engagement of the internal and external threads, pusher pins adapted to be pushed by the cartridge holder for moving the locking ring from the forward position to the rearward position when the cartridge holder is inserted in and coupled to the cylindrical space, and a coil spring for pushing the locking ring back to the forward position when the cartridge holder is not in the cylindrical space, the rotation of the rotating cylinder body resulting in rotative motion of the nut around the plunger rod to linearly move forward the plunger rod.

According to the invention, the externally threaded plunger rod preferably has opposite flat sides formed thereon parallel to the longitudinal axis thereof, and a guide bore is formed in the casing with a configuration in section conformed to that of the plunger rod, the non-rotation and longitudinal movement of the plunger rod being accomplished by passing it through the guide bore.

The arm-like nut halves preferably have outer arc surfaces each with an inclined arcuate surface formed at the forward protrusive ends thereof and longitudinally parallel flat surfaces. The arm-like nut halves are also located in a slot formed in a forward portion of the rotating cylinder body and pivotally connected to the rotating cylindrical body by means of pivot pins.

The locking ring preferably includes an inner cylindrical bore in which the forward protrusions of the arm-like nut halves are received, and an inclined cam surface to engage corresponding inclined arcuate surfaces on the outer arc surfaces of the arm-like nut halves in the rearward position of the locking ring, and is provided at its forward end with a thrust bearing for rotational contact with rear end faces of the pusher pins. The coil spring has one end abutting lugs formed on the arm-like nut halves at their rear ends and another end abutting a seat formed on the locking ring at its rear end, so that the locking ring is urged toward its forward position and the arm-like nut halves are urged radially outwardly about the pivot pins to permit the internal threads on the nut halves to disengage from the external threads on the plunger rod.

In a preferable embodiment of the invention, there is provided a power transmission mechanism for transmitting the rotation of the drive shaft to the rotating cylindrical body. the power transmission mechanism including opposite flat cam surfaces formed on the drive shaft at is forward end, an outer annular groove formed on the rotating cylindrical body at its rear end, an aperture formed in the outer annular groove, a locking ball received in the aperture and a split circular torque band consisting of a leaf spring fitted in the outer annular groove for urging the locking ball toward the flat cam surface.

EMBODIMENT FOR CARRYING OUT THE INVENTION

Figure 1:
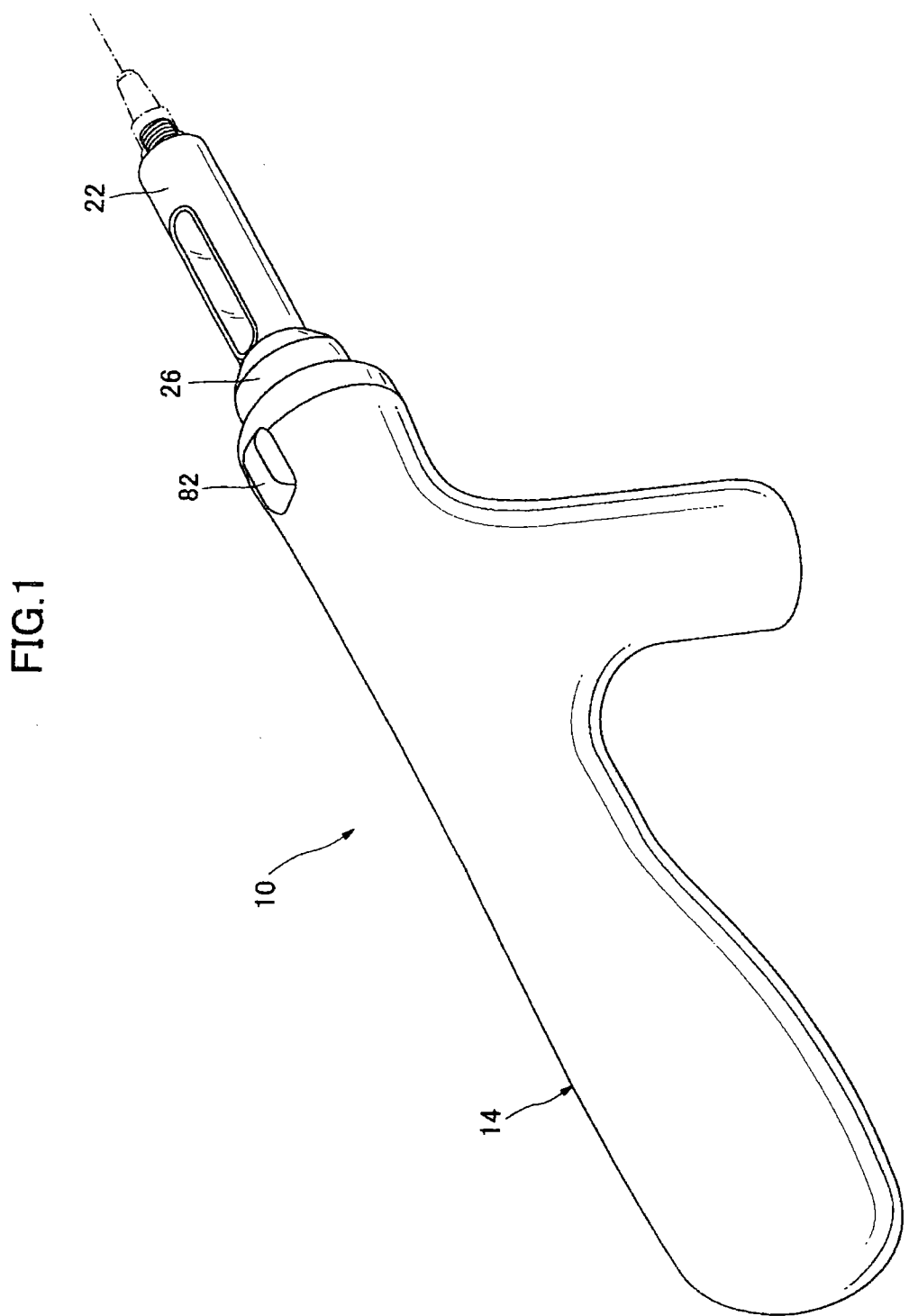
FIG. 1 is a perspective view of an entire linear cartridge-type motorized dental syringe embodying the present invention.
Figure 2:
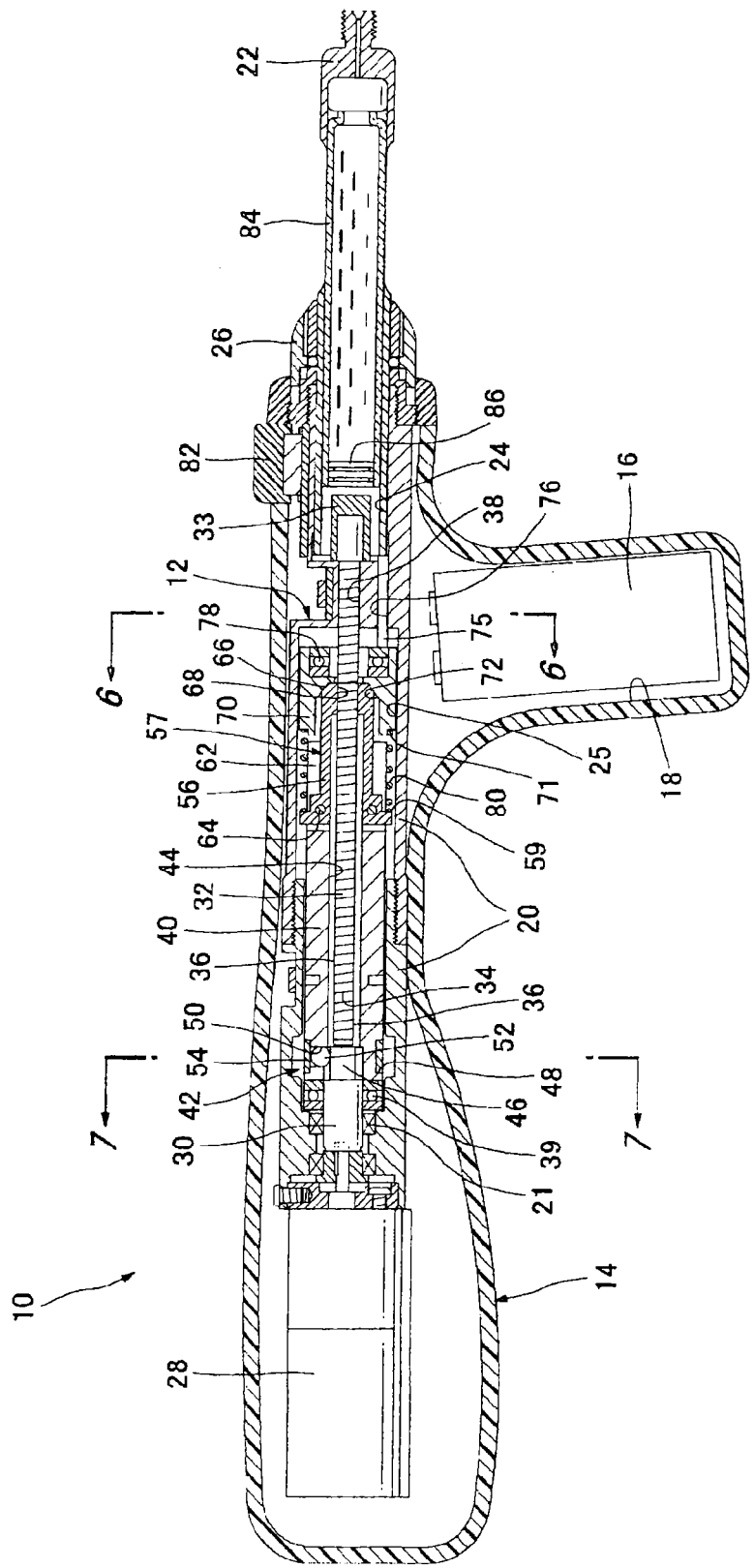
FIG. 2 is a longitudinal cross-sectional view of the cartridge-type motorized dental syringe shown in FIG. 1.

Referring to the accompanying drawings, particularly, FIGS. 1 and 2 therein, a linear cartridge-type motorized dental syringe is generally indicated by reference numeral 10 and comprises a motorized syringe unit 12 and a housing 14 in which the motorized syringe unit 12 is incorporated, the housing 14 including a battery box 18 adapted to contain a battery 16 therein. The motorized syringe unit 12 also includes a fixed casing 20 having at its front end a cylindrical space 24 for inserting a cartridge holder 22 therein and a coupling 26 for detachably connecting the inserted cartridge holder 22 to the cylindrical space 24. A motor with a reduction gear (referred to as a geared motor) 28 is secured to rear end of the casing 20. A drive shaft 30 is fixedly connected to a spindle of the geared motor 28 and rotatably supported in a bearing 21 mounted in the casing 20. An externally threaded plunger rod 32 is located in the casing longitudinally of the syringe in alignment with an axis of the drive shaft 30. The plunger rod 32 includes a head 33 secured to the tip end thereof, external threads 34 formed thereon throughout the length of the plunger rod 32 and having an extremely short pitch and opposite flat sides 36 formed on the plunger rod parallel to the longitudinal axis of the plunger rod. A guide bore 38 is formed in the casing 20 to linearly guide the plunger rod. To this end, the section of the guide bore 38 has a configuration in conformity to that of the plunger rod and namely, the guide bore has opposite arced surfaces and opposite parallel sides. Thus, non-rotation and longitudinal movement of the plunger rod 32 can be accomplished by passing it through the guide bore 38 (see FIG. 6). A rotating cylindrical body 40 is located coaxially in the casing 20, connected through a power transmission mechanism 42 to the drive shaft 30 of the geared motor, and has a longitudinal bore 44 in which the plunger rod is received coaxially. There is provided a thrust bearing indicated by reference numeral 39 making rotational contact with an end face of the rotating cylindrical body 40 possible.

Figure 3:
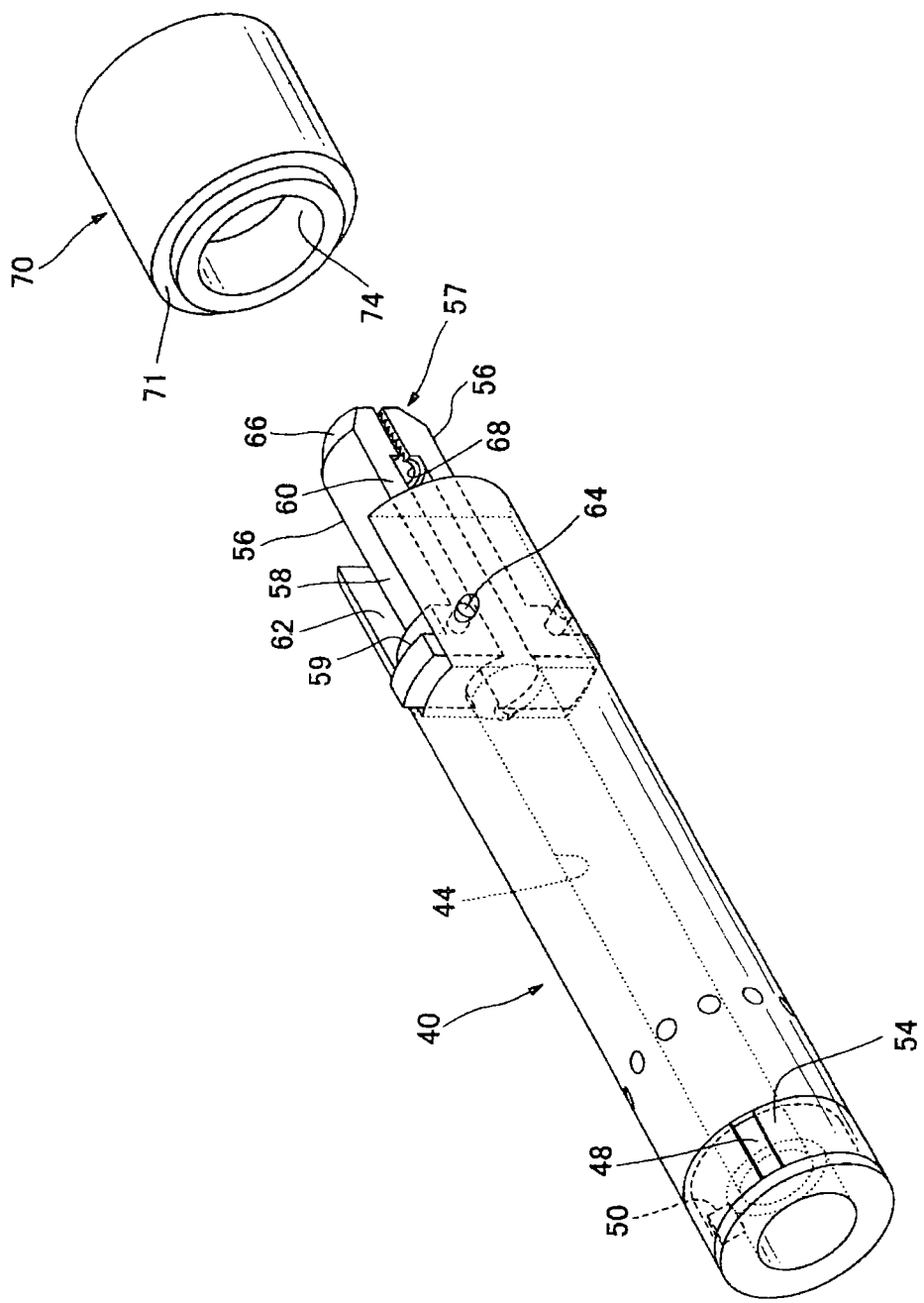
FIG. 3 is a perspective view of a locking ring and rotating cylindrical body with a nut comprising arm-like nut halves mounted thereon.
Figure 7:
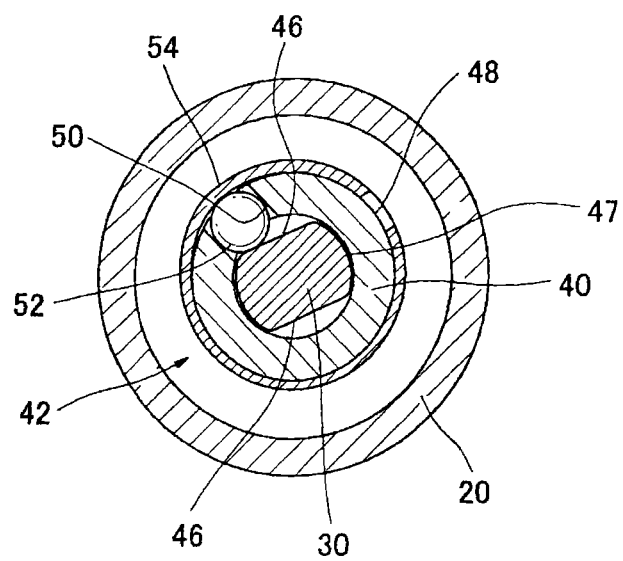
FIG. 7 is a cross-sectional view of the syringe taken along line 7-7 in FIG. 2.

Referring to FIGS. 2, 3 and 7, the power transmission mechanism 42 includes opposite flat cam surfaces 46 formed on the drive shaft 30 at its forward end, an outer annular groove 48 formed on the rotating cylindrical body 40 at its rear end, an aperture 50 formed in the outer annular groove 48, a locking ball 52 received in the aperture 50, and a split circular torque band 54 consisting of a leaf spring and fitted in the outer annular groove 48. When the syringe is in use, the flat cam surface 46 on the drive shaft 30 engages the locking ball 52 at a point thereon adjacent one of outer arc surfaces (that is to say, a point on the flat cam surface having a larger radius from the axis of the drive shaft 30) to push the locking ball 52 against the split circular torque band 54, thereby expanding it. The expansion of the split circular torque band 54 results in production of a spring action under which the locking ball 52 is pressed against the flat cam surface 46 at that point. Thus, the drive shaft 30 is operatively connected to the rotating cylindrical body 40 to transmit rotation of the drive shaft 30 to the rotating cylindrical body 40. When overload is produced enough to stop the rotation of the rotating cylindrical body 40, a relative rotational movement between the rotating cylindrical body 40 and the drive shaft 30 of the geared motor 28 takes place. The outer arc surface 47 on the drive shaft 30 is brought into rolling contact with the locking ball 52 against the spring action of the split circular torque band 54 and then, the flat cam surface 46 on the drive shaft 30 faces the locking ball 52 to relieve the spring action of torque band 54 so that the locking ball 54 falls onto the flat cam surface 46. Such actions in series result in continuous idling motion of the drive shaft 30 relative to the rotating cylindrical body 40 without transmitting the rotation of the drive shaft to the rotating cylindrical body 40.

Figure 4:
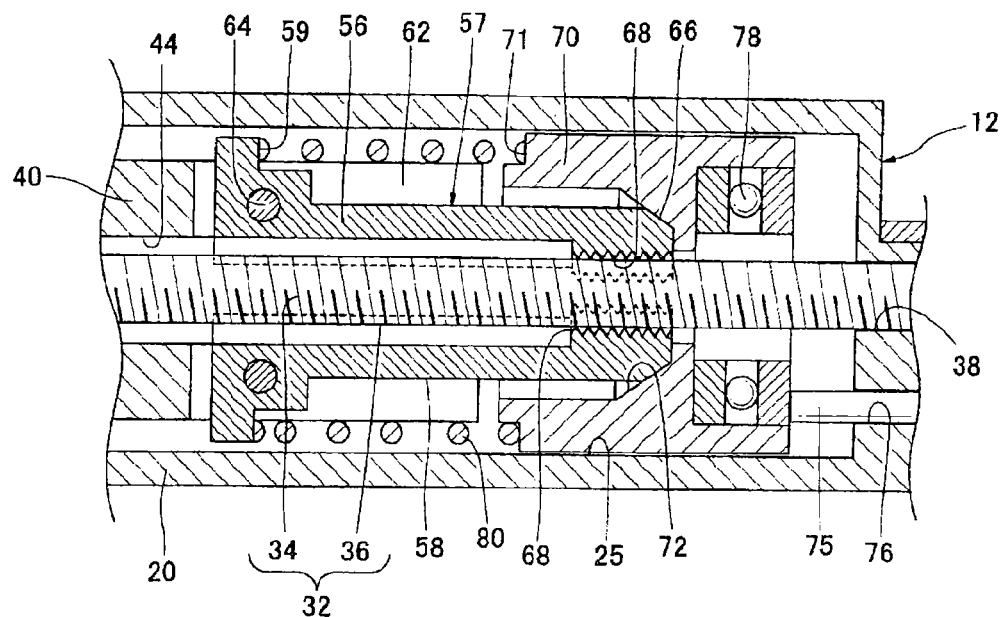
FIG. 4 is a fragmental vertical cross-sectional view of the dental syringe illustrating the nut and the locking ring shown in FIG. 3.
Figure 5:
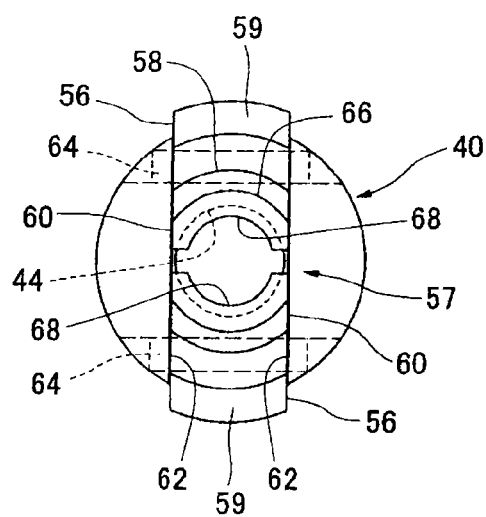
FIG. 5 is a front view of the nut and locking ring shown in FIG. 3.

As will be seen in FIGS. 3, 4 and 5, a nut 57 includes a pair of opposite arm-like nut halves 56 and is mounted on the rotating cylindrical body 40. Each of the arm-like nut halves 56 has outer arc surface 58 and longitudinally parallel flat surfaces 60 and thanks to the flat surfaces, is located in a longitudinally extending slot 62 formed in a forward portion of the rotating cylindrical body 40, for non-rotation. Each arm-like nut half 56 is pivotally connected to rotating cylindrical body 40 by a cross pivot pin 64, and has a dimension projecting forwardly beyond the forward end of the rotating cylindrical body 40, and includes an inclined arcuate surface 66 on the forward end of the nut half and internal threads 68 formed on an inner surface of the nut half and adapted to engage or mesh with the external threads 34 on the plunger rod 32. There is provided a locking ring 70 having an inner cylindrical bore 74 with a inclined cam surface 72 adapted to engage the inclined arcuate surface 66 on the arm-like nut half 56 when the forward protrusions of the arm-like nut halves 56 are received in the bore 74. The locking ring 70 is located in the fixed casing 20 on the cylindrical surface 25 for rotation and for longitudinal movement between a rearward position, and a forward position. In the rearward position, the inclined cam surface 72 engages the inclined arcuate surfaces 66 on the arm-like nut halves 56 to perform pivotal movement of the arm-like nut halves 56 around the pivot pins 64 toward the plunger rod 32, thereby meshing the internal threads 68 on the arm-like nut halves 56 with the external threads 34 on the plunger rod 32. In the forward position, the inclined cam surface 72 is disengaged from the inclined arcuate surfaces 66 on the arm-like nut halves 56 to release the meshing of the internal threads 68 with the external threads 34 on the plunger rod 32.

Figure 6:
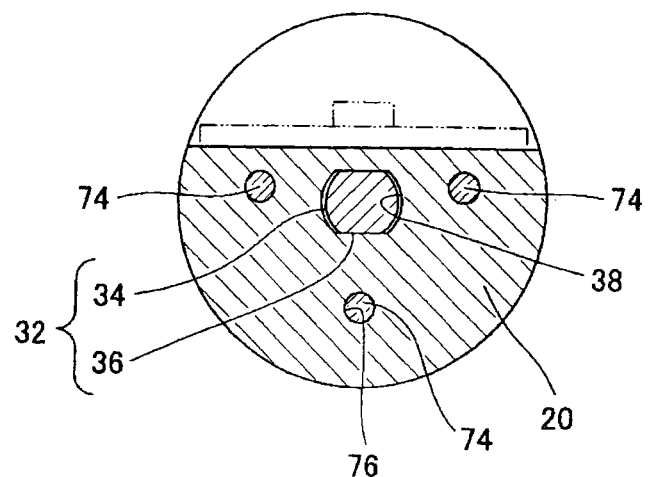
FIG. 6 is a cross-sectional view of the syringe taken along line 6-6 in FIG. 2.

As shown in FIGS. 2 and 6, a plurality of pusher pins 75 each is received in one of corresponding pin holes 76 formed in the fixed casing 20 at a angularly equal spacing, and each pusher pin 75 has a length such that when the cartridge holder 22 is inserted into and coupled to the cylindrical space 24, the pusher pin 75 is pushed by the rear end of the cartridge holder 22 to move the locking ring 70 from the forward position to the rearward position. The locking ring 70 is preferably provided at its forward end with a thrust bearing 78 to rotatively contact with the end faces of the pusher pins 75. There is provided a coil spring 80 for urging the locking ring 70 toward its forward position when the cartridge holder 22 is not in the cylindrical space 24. The coil spring has one end abutting lugs 59 formed on the arm-like nut halves 56 at their rear ends, and another end abutting a seat 71 formed on the locking ring 70 at its rear end so that when the locking ring 70 is in its forward position, the arm-like nut halves 56 are urged radially outwardly around the pivot pins 64 to disengage the internal threads 68 from the threads 34 on the plunger rod 32.

Reference numeral 82 indicates a switch for actuating the geared motor 28. The housing may preferably be made of plastic material while the above-described parts of the motorized dental syringe are of metallic materials.

Operation of the motorized dental syringe is described herein below. It is assumed that, due to the fact that the cartridge holder 22 is not in the cylindrical space 24 in the fixed casing 20, the locking ring 70 is in its forward position wherein the pusher pins 75 are pushed forwardly to a ready position in the cylindrical space 24 of the fixed casing 20. and that the plunger rod 32 is retracted to its initial position. Operation of the coupling 26 permits the cartridge holder having an anesthetic filled cartridge received therein to be inserted in and coupled to the cylindrical space in the fixed casing 20. The pusher pins 75 are pushed rearward by the rear end of the cartridge holder 22 to move the locking ring 70 from its forward position to its rearward position against the action of the coil spring 80. The inclined cam surface 72 engages the inclined arcuate surfaces 66 on the arm-like nut halves 56 to pivot the arm-like nut halves 56 toward the plunger rod 32 around the pivot pins 64, thereby meshing the internal threads 68 on the arm-like nut halves 56 with the external threads 34 on the plunger rod 32. Prior to operation of injection, it will be apparent that a dental double-edged needle (shown in a phantom line in FIG. 1) is mounted on the cartridge holder 22 with it penetrating a cartridge 84. The geared motor is actuated by operating the switch 82 such that rotation of the geared motor 28 is transmitted through the drive shaft 30 and the power transmission mechanism 42 to the rotating cylindrical body 40 to rotate the nut 57 around the plunger rod 32, thereby moving linearly the plunger rod at extremely low speed. Thus a rubber plunger 86 in the cartridge 84 is pushed by the moving plunger rod 32 so that anesthetic can be ejected through the needle.

If overload should take place in the syringe, the drive shaft 30 performs idling motion relative to the rotating cylindrical body 40 as described above so that any rotation is not transmitted to the rotating cylindrical body. Rotation of the drive shaft 30 permits the outer arc surface 47 on the drive shaft 30 to contact the locking ball 52 for production of spring action of split circular torque band 54 under which the locking ball 52 is urged radially inwardly and ultimately, the locking ball 52 falls onto the flat cam surface 46. Whenever such actions in series are repeated, the power transmission mechanism make a noise due to mutual contact of metals, so that the user can know that the syringe is in an abnormal state. Thus, the switch 82 is operated to stop the actuation of the geared motor 28.

Upon completion of the operation of injection, the coupling 26 is operated to pull the cartridge holder 22 out of the cylindrical space 24. Then, pushing of the pusher pins 75 is released, and the locking ring 70 is pushed back from the rearward position to the forward position under the action of coil spring 80. The action of the spring 80 permits the arm-like nut halves 56 to be pivoted radially outwardly around the pivot pins 64, whereby the internal threads 68 on the arm-like nut halves 56 are disengaged from the external threads on the plunger rod 32. Thus, a plastic tool (not shown) may be used to return freely the forward moved plunger rod to its initial position by hand.

According to the invention, since the nut is rotated around the plunger rod to move it linearly by the action of a screw, any specific reduction gear is not required for further reducing the speed of revolution of the geared motor.

What is claimed is:

1. A linear cartridge-type motorized dental syringe, comprising: a housing in which a motorized syringe unit is fixedly incorporated, the motorized syringe unit comprising a casing provided with a coupling having, at a front end thereof, a cylindrical space in which a cartridge holder is inserted, the coupling functioning to detachably couple the inserted cartridge holder to the syringe unit, and a motor comprising a reduction gear, said geared motor being secured to a rear end of a fixed casing, an externally threaded plunger rod located in alignment with an axis of a drive shaft of the geared motor, the plunger rod being movable longitudinally of the casing but not rotatable relative to the casing, a rotating cylindrical body located coaxially in the casing and operatively connected to the drive shaft of the geared motor such that it can be rotated by the drive shaft, a nut including a pair of arm-like nut halves protrusive forward beyond a forward end of the rotating cylindrical body and having, on forward inner surfaces of the nut halves, internal threads adapted to engage external threads on the plunger rod, a locking ring located for rotation around a longitudinal axis of the plunger rod and for longitudinal movement between a rearward position wherein the locking ring forces the internal threads on the arm-like nut halves to engage the external threads on the plunger rod, and a forward position wherein the locking ring releases the mutual engagement of the internal and external threads, pusher pins adapted to be pushed by the cartridge holder for moving the locking ring from the forward position to the rearward position when the cartridge holder is inserted in and coupled to the cylindrical space, and a coil spring for pushing the locking ring back to the forward position when the cartridge holder is not in the cylindrical space, the rotation of the rotating cylinder body resulting in rotative motion of the nut around the plunger rod to linearly move forward the plunger rod.

2. The linear cartridge-type motorized dental syringe as claimed in claim 1, wherein the arm-like nut halves have outer arc surfaces each with an inclined arcuate surface formed at forward protrusive ends thereof and longitudinally parallel flat surfaces, and the arm-like nut halves are located in a slot formed in a forward portion of the rotating cylinder body and pivotally connected to the rotating cylindrical body by means of pivot pins.

3. The linear cartridge-type motorized dental syringe as claimed in claim 2, wherein the locking ring includes an inner cylindrical bore in which the forward protrusive ends of the arm-like nut halves are received, and an inclined cam surface to engage corresponding inclined arcuate surfaces on the outer arc surfaces of the arm-like nut halves in the rearward position of the locking ring.

4. The linear cartridge-type motorized dental syringe as claimed in claim 3, wherein the locking ring is provided at its forward end with a thrust bearing for rotational contact with rear end faces of the pusher pins.

5. The linear cartridge-type motorized dental syringe as claimed in claim 1, wherein the externally threaded plunger rod has opposite flat sides formed thereon parallel to the longitudinal axis thereof, and a guide bore is formed in the casing with a configuration in section conformed to that of the plunger rod, the non-rotation and longitudinal movement of the plunger rod being accomplished by passing the plunger rod through the guide bore.

6. The linear cartridge-type motorized dental syringe as claimed in claim 1, wherein the coil spring has one end abutting lugs formed on the arm-like nut halves at their rear ends, and another end abutting a seat formed on the locking ring at its rear end, such that the locking ring is urged toward its forward position and the arm-like nut halves are urged radially outwardly about the pivot pins to permit the internal threads on the nut halves to disengage from the external threads on the plunger rod.

7. The linear cartridge-type motorized dental syringe as claimed in claim 1, further comprising a power transmission mechanism for transmitting the rotation of the drive shaft to the rotating cylindrical body, the power transmission mechanism including opposite flat cam surfaces formed on the drive shaft at its forward end, an outer annular groove formed on the rotating cylindrical body at its rear end, an aperture formed in the outer annular groove, a locking ball received in the aperture and a split circular torque band consisting of a leaf spring fitted in the outer annular groove for urging the locking ball toward the flat cam surface.

* * * * *